(12) United States Patent
Hernandez

(10) Patent No.: US 12,350,351 B2
(45) Date of Patent: Jul. 8, 2025

(54) TOPICAL VITAMIN C COMPOSITION

(71) Applicant: Topix Pharmaceuticals, Inc., N. Amityville, NY (US)

(72) Inventor: Steven Hernandez, Blue Point, NY (US)

(73) Assignee: Topix Pharmaceuticals, Inc., N. Amityville, NY (US)

( * ) Notice: Subject to any disclaimer, the term of this patent is extended or adjusted under 35 U.S.C. 154(b) by 46 days.

(21) Appl. No.: 17/362,204

(22) Filed: Jun. 29, 2021

(65) Prior Publication Data

US 2021/0401682 A1 Dec. 30, 2021

Related U.S. Application Data

(60) Provisional application No. 63/045,409, filed on Jun. 29, 2020.

(51) Int. Cl.
| | |
|---|---|
| *A61K 8/06* | (2006.01) |
| *A61K 8/34* | (2006.01) |
| *A61K 8/67* | (2006.01) |
| *A61Q 19/02* | (2006.01) |
| *A61Q 19/08* | (2006.01) |

(52) U.S. Cl.
CPC .............. *A61K 8/062* (2013.01); *A61K 8/676* (2013.01); *A61Q 19/02* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| | | | | |
|---|---|---|---|---|
| 4,818,521 | A * | 4/1989 | Tamabuchi | ............ A61Q 19/00 514/474 |
| 9,056,209 | B2 * | 6/2015 | Sugiyama | ............... A61K 8/498 |
| 9,326,932 | B2 | 5/2016 | Lewis, II et al. | |
| 9,440,098 | B2 | 9/2016 | Sachdev | |
| 9,713,604 | B2 | 7/2017 | Dreher | |
| 2002/0028844 | A1 * | 3/2002 | Fitzpatrick | ............. A61Q 19/00 514/474 |
| 2007/0243271 | A1 * | 10/2007 | Hernandez | ............. A61K 36/82 424/195.18 |
| 2010/0069476 | A1 | 3/2010 | Hara et al. | |
| 2012/0213842 | A1 * | 8/2012 | Birbara | ................... A61P 17/16 424/59 |
| 2014/0315995 | A1 * | 10/2014 | Dreher | ................... A61P 39/06 514/458 |
| 2020/0030201 | A1 * | 1/2020 | Murakoso | ................ A61K 8/44 |
| 2020/0188292 | A1 | 6/2020 | Carle et al. | |

FOREIGN PATENT DOCUMENTS

| | | |
|---|---|---|
| CN | 105979924 A | 9/2016 |
| WO | 03009825 A2 | 2/2003 |
| WO | 03009825 A3 | 4/2003 |
| WO | 2008140065 A2 | 11/2008 |
| WO | 2020081983 A1 | 4/2020 |

OTHER PUBLICATIONS

Choi, S., et al. Int. J. Mol. Med. (2016), 38; 627-634.*
Epstein, H. "Skin Care Products." in Handbook of Cosmetic Science and Technology, 3rd Edition (2009) 121-134. (Year: 2009).*
Weber, S.U., et al. "Antioxidants." in Handbook of Cosmetic Science and Technology, 3rd Edition (2009) 301-310. (Year: 2009).*
International Search Report for PCT/US2021/039388 mailed Oct. 14, 2021, 13 pages.
Scalia et al., "Comparative evaluation of different co-antioxidants on the photochemical and functional stability of epigallocatechin-3-gallate in topical creams exposed to simulated sunlight." Molecules, vol. 18, Issue 1, pp. 574-587, 2013.
Chen et al., "Stabilizing Effect of Ascorbic Acid on Green Tea Catechins" Journal of Agricultural and food Chemistry, vol. 46, Issue 7, pp. 2512-2516.
Extended European Search Report for European Application No. 21838714.0, mailed Sep. 23, 2024, 12 Pages.
Jagdeo J., et al., "Novel Vitamin C and E and Green Tea Polyphenols Combination Serum Improves Photoaged Facial Skin," Journal of Drugs in Dermatology, Sep. 1, 2021, vol. 20(9), pp. 996-1003.
Office Action for Chinese Patent Application No. 202180055869.4, mailed Sep. 23, 2024, 28 Pages.
Zhang et al., "Practical Cosmetic Drugs," Huazhong University of Science and Technology Press, Aug. 31, 2016, p. 113.

* cited by examiner

*Primary Examiner* — Bethany P Barham
*Assistant Examiner* — Peter Anthopolos
(74) *Attorney, Agent, or Firm* — Lowenstein Sandler LLP

(57) ABSTRACT

Disclosed in certain embodiments herein is a topical composition that delivers advanced environmental protection to the skin, brightens the complexion of the skin, and/or delivers anti-aging benefits to the skin by treating intrinsic and/or extrinsic factors associated with the appearance and health of the skin. The topical composition may be an emulsion of an aqueous phase and an oily phase, or other two-phase system, that includes an ascorbate component and an antioxidant system that includes green tea polyphenols. Also disclosed herein are methods of administering the topical compositions described herein for treating a skin of a subject for effects of radical induced damage, atmospheric aging, and as part of a variety of dermatological procedures.

15 Claims, 3 Drawing Sheets

TOPICAL VITAMIN C COMPOSITION

CROSS REFERENCE TO RELATED APPLICATION(S)

The present application claims priority to U.S. Provisional Application No. 63/045,409 filed on Jun. 29, 2020, which is incorporated by reference in its entirety.

FIELD OF THE INVENTION

The present invention relates to cosmetic compositions for skin care applications.

BACKGROUND OF THE INVENTION

Overexposure to the sun and other toxic free radical sources and irritants induces skin damage, resulting in a variety of disfiguring skin conditions. Among these skin conditions, wrinkles, fine lines, loss of elasticity, sagging, dryness, age spots are caused by sun damage and aging. Wrinkles of the skin are either deep furrows and creases or fine lines. Wrinkles can occur on any part of the body, but especially where sun exposure is greatest, such as on the face, neck, forearms and hands.

Free radicals from ultraviolet light (UV) are known to increase with air pollution in areas of concentrated populations, thereby magnifying the problem. The free radicals are destructive in that the free radicals hydrolyze elastin fibers in the skin and synthesize collagen in the lower dermal layers of the skin, thereby causing skin wrinkles and other damaging skin conditions.

Nowadays, individuals often seek means for preventing and/or counteracting effects of aging and sun exposure. A variety of cosmetic compositions as well as homeopathic and prescription remedies are available to the consumer looking achieve a more youthful and healthy appearance. However, there remains a need for topical compositions that provide effective treatment and preventative measures against skin photo-aging and related skin disorders.

SUMMARY

It is an object of certain embodiments of the disclosure to provide a topical composition, a method of preparing, and a method of using said topical composition for protecting against atmospheric or extrinsic aging.

It is an object of certain embodiments of the disclosure to provide a topical composition, a method of preparing, and a method of using said topical composition for reducing, attenuating, minimizing, treating premature signs of aging caused by free radicals, reactive oxygen species (ROS) from IRA, UVA, UVB, REV (blue) light, IR, pollution, allergens, irritants, or intrinsic sources and the like.

It is an object of certain embodiments of the disclosure to provide a topical composition, a method of preparing, and a method of using said topical composition as part of a regimen pre dermatological procedures or post dermatological procedures (such as non-ablative dermatological procedures, chemical peels, micro-abrasion, and laser).

It is an object of certain embodiments of the disclosure to provide a topical composition for improving the appearance of the skin, skin elasticity, body firming or to reduce the visible signs of photo-aged skin, sunburn, wrinkles, and related skin disorders.

One or more of the above objects and others may be met in the instant disclosure which in certain embodiments is directed to a topical composition that includes an emulsion of an aqueous phase and an oily phase, where the topical composition includes an ascorbate component and above 0 wt. % to about 10 wt. % of an antioxidant system that includes green tea polyphenols.

In certain embodiments, the instant disclosure is directed to a method of treating the skin of a subject for effects of radical-induced damage, a method of brightening the skin of a subject, a method of treating the skin of a subject for effects of atmospheric or actinic aging, or as part of a treatment regimen with certain dermatological procedures. These methods include administering, to the skin of the subject, any of the topical compositions described herein.

In certain embodiments, the instant disclosure is directed to composition and method of treating skin of a subject for effects of atmospheric aging, wherein the skin exhibits improvement in appearance of fine lines on the eye area, smoothness, and radiance of the skin.

In certain embodiments, the instant disclosure is directed to composition and method of treating skin of a subject, wherein the skin exhibits at least one of reduction or attenuation of fine lines on the eye area; an increase or maintenance of smooth skin; an increase or maintenance of radiance; a decrease or maintenance of wrinkles on the global face; a decrease or maintenance of wrinkles on the eye area; a reduction or maintenance of hyperpigmentation; and an increase or maintenance of firmness.

In certain embodiments, the instant disclosure is directed to composition and method of treating skin of a subject, wherein the skin exhibits when tested according to a Modified Griffiths 10-Point Scale an improvement compared to baseline at weeks 4, 8 and/or 12 of at least one of fine lines of the eye; skin smoothness; radiance; wrinkles on the global face; wrinkles on the eye area; hyperpigmentation; and firmness.

In certain embodiments, the instant disclosure is directed to composition and method of treating skin of a subject, wherein the skin exhibits when tested according to a Modified Griffiths 10-Point Scale at an improvement compared to baseline of at least one of −5% to −25%, −15% to −35% or −25% to −45% at weeks 4, 8 and 12 respectively for fine lines of the eye.

In certain embodiments, the instant disclosure is directed to composition and method of treating skin of a subject, wherein the skin exhibits when tested according to a Modified Griffiths 10-Point Scale at an improvement compared to baseline of at least one of −1% to −10%, −5% to −15% or −10% to −20% at weeks 4, 8 and 12 respectively for skin smoothness.

In certain embodiments, the instant disclosure is directed to composition and method of treating skin of a subject, wherein the skin exhibits when tested according to a Modified Griffiths 10-Point Scale at an improvement compared to baseline of at least one of −1% to −10%, −3% to −13% or −5% to −15% at weeks 4, 8 and 12 respectively for radiance.

In certain embodiments, the instant disclosure is directed to composition and method of treating skin of a subject, wherein the skin exhibits when tested according to a Modified Griffiths 10-Point Scale at an improvement compared to baseline of at least one of −1% to −10% or −3% to −13% at weeks 4 and 12 respectively for wrinkles on the global face.

In certain embodiments, the instant disclosure is directed to composition and method of treating skin of a subject, wherein the skin exhibits when tested according to a Modified Griffiths 10-Point Scale at an improvement compared to baseline of at least one of −1% to −10% or −2% to −12% at weeks 4 and 12 respectively for wrinkles on the eye area.

In certain embodiments, the instant disclosure is directed to composition and method of treating skin of a subject, wherein the skin exhibits when tested according to a Modified Griffiths 10-Point Scale at an improvement compared to baseline of at least one of −1% to −10% or −5% to −15% at weeks 4 and 12 respectively for hyperpigmentation.

In certain embodiments, the instant disclosure is directed to composition and method of treating skin of a subject, wherein the skin exhibits when tested according to a Modified Griffiths 10-Point Scale at an improvement compared to baseline of at least one of −1% to −10% or −3% to −13 at weeks 4 and 12 respectively for firmness.

In certain embodiments, the instant disclosure is directed to composition and method of treating skin of a subject, wherein at least 50% of subjects, at least 60% of subjects, at least 70% of subjects, at least 80% of subjects, at least 90% of subjects or at least 95% of subjects exhibit when tested according to a Modified Griffiths 10-Point Scale at an improvement compared to baseline in at least one of fine lines of the eye; skin smoothness; radiance; wrinkles on the global face; wrinkles on the eye area; hyperpigmentation; and firmness.

The term "administering the topical composition" as used herein refers to applying topically onto a skin of a subject, e.g., on the face, neck, hands, feet, elbows, knees, and the like. As used herein, the terms "application," "apply," and "applying" with respect to a disclosed topical formulation or method of using a disclosed topical formulation, refer to any manner of administering a topical formulation to the skin, for example, the skin of a person, such as the skin of a patient, which, in medical or cosmetology practice, delivers the formulation to the subject's skin surface. Smearing, rubbing, spreading, spraying a disclosed topical formulation, with or without the aid of suitable devices, on a subject's skin are all included within the scope of the term "application," as used herein. The term "topical" or "topically" with respect to administration or application of a disclosed skincare formulation refers to epicutaneous administration or application, onto skin. The application can be manually (e.g., directly with the hands) or manipulated with an applicator, cloth, device, roll-on, wipes, unit dose sponge applicators, liquid applied with swabs or cotton balls, impregnated gauze or other substrates, coated silicone sheets or other sheet goods, coated bandages or externally fixed devices, towelettes, individually packages pledgettes or pads, transdermal delivery system, etc. Administration can be self-administration or administration by a medical professional or caregiver.

In certain embodiments, the instant disclosure is directed to a method of preparing any of the topical compositions described herein by combining an ascorbate component and above 0 wt. % to about 10 wt. % of an antioxidant system that includes green tea polyphenols.

DETAILED DESCRIPTION

Figure 1:
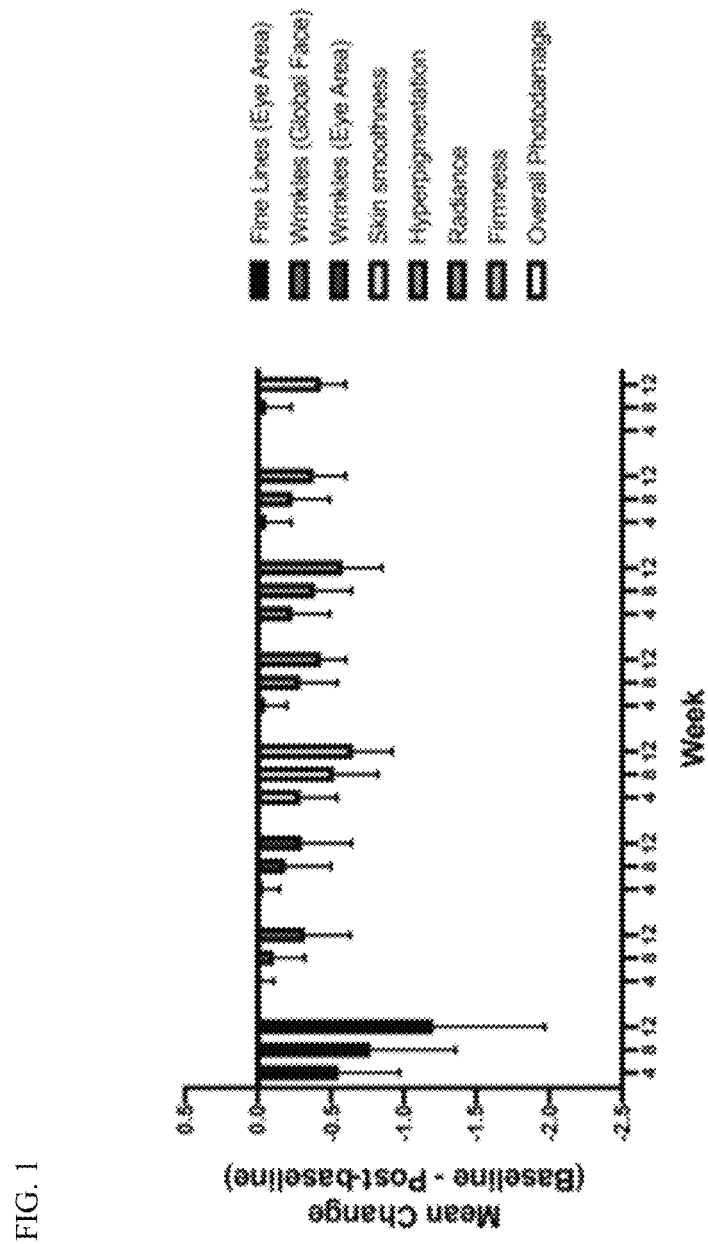
FIG. 1 is a summary of the improvements across all clinical efficacy parameters of the Clinical Study of Example 2.

The following definitions are used, unless otherwise described.

The term "alkyl" as used herein refers to straight and branched hydrocarbon groups. Reference to an individual radical such as propyl embraces only the straight chain radical, a branched chain isomer such as isopropyl being specifically referred to.

The term "halo" or "halogen" as used herein refers to fluoro, chloro, bromo and iodo.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocycles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, spiro[4.5]decane, etc.), via two adjacent carbon atoms to form a fused connection such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane) or via two non-adjacent carbon atoms to form a bridged connection (e.g. norbornane, bicyclo[2.2.2]octane, etc.). The "carbocycle" or "carbocyclyl" may also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl and cycloheptyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

As used herein, "free or substantially free," refers to a topical composition that comprises less than about 1 wt. %, less than about 0.5 wt. %, less than about 0.25 wt. %, less than about 0.1 wt. %, less than about 0.05 wt. %, less than about 0.01 wt. %, or 0 wt. % of said component.

Topical Composition

According to various embodiments, the present disclosure is related to a topical composition that is an emulsion of an aqueous phase and an oily phase. The topical composition includes an ascorbate component and an antioxidant system that includes green tea polyphenols. In certain embodiments, the topical composition further includes at least one additional cosmetically acceptable excipient.

The ascorbate component in any of the topical compositions described herein can include ascorbic acid, or its derivatives, such as ascorbyl palmitate, sodium ascorbate, potassium ascorbate, ammonium ascorbate, triethanolamine ascorbate, ascorbyl phosphate or magnesium ascorbyl phosphate, ascorbic acid polypeptides, ascorbyl glucosamine, ascorbic acid polymers, esters of ascorbic acid, amides of ascorbic acid, L-ascorbic acid, tetrahexyldecyl ascorbate, known as vitamin C, or other derivatives, or related compounds, including botanical or herbal extracts, such as extracts of acerola, citrus extracts, strawberry, which may supply L-ascorbic acid or its derivatives. In certain embodiments, the ascorbate component in the topical composition includes ascorbic acid, tetrahexyldecyl ascorbate, or a combination thereof.

The ascorbate component in any of the topical compositions described herein may be present in a concentration of from any of about 0.1 wt. %, about 1 wt. %, about 5 wt. %, about 10 wt. %, about 12 wt. %, about 15 wt. %, about 18%, about 20 wt. %, about 23 wt. %, or about 25 wt. % to any of about 28 wt. %, about 30 wt. %, about 35 wt. %, about 40 wt. %, about 45 wt. %, about 50 wt. %, about 75 wt. %, or about 95 wt. %, based on total weight of the topical composition. In certain embodiments, the ascorbate component is present in any of the topical compositions described herein in an amount ranging from about 5 wt. % to about 40 wt. %, from about 10 wt. % to about 30 wt. %, or from about 15 wt. % to about 25 wt. %, based on total weight of the topical composition.

In certain embodiments, the ascorbate component includes ascorbic acid (e.g., L-ascorbic acid) in the topical composition in an amount ranging from about 2 wt. % to about 30 wt. %, from about 5 wt. % to about 25 wt. %, from about 10 wt. % to about 30 wt. %, or from about 10 wt. % to about 20 wt. %, based on total weight of the topical composition.

In certain embodiments, the ascorbate component includes tetrahexyldecyl ascorbate in the topical composition in an amount ranging from about 1 wt. % to about 20 wt. %, from about 1 wt. % to about 15 wt. %, from about 2 wt. % to about 20 wt. %, from about 2 wt. % to about 10 wt. %, or from about 3 wt. % to about 7 wt. %, based on total weight of the topical composition.

In certain embodiments, the ascorbate component in the topical composition includes, comprises, consists, or consists essentially of L-ascorbic acid in combination with tetrahexyldecyl ascorbate in an (individual or cumulative) concentration of from any of about 0.1 wt. %, about 1 wt. %, about 5 wt. %, about 10 wt. %, about 12 wt. %, about 15 wt. %, about 18 wt. %, about 20 wt. %, about 23 wt. %, or about 25 wt. % to any of about 28 wt. %, about 30 wt. %, about 35 wt. %, about 40 wt. %, about 45 wt. %, about 50 wt. %, about 75 wt. %, or about 95 wt. %, by weight, based on total weight of the topical composition.

In certain embodiments, the ascorbate component comprises, consists, or consists essentially of L-ascorbic acid in combination with tetrahexyldecyl ascorbate in a weight to weight ratio of the L-ascorbic acid to the tetrahexyldecyl ascorbate from about 10:1 to about 1:10, about 8:1 to about 1:8, about 5:1 to about 1:5, about 3:1 to about 1:3, about 3:1 to about 1:1, about 5:1 to about 1:1, about 8:1 to about 1:1, or about 10:1 to about 1:1.

Certain plants, such as green tea, that are composed of a high content of polyphenols which are bioflavonoids and have antioxidant properties are included in any of the topical compositions described herein. The antioxidant system in the topical compositions described herein may be present in a concentration of from any of above 0%, about 0.01 wt. %, about 0.05 wt. %, about 0.1 wt. %, about 0.15 wt. %, about 0.2 wt. %, about 0.25 wt. %, about 0.3 wt. %, about 0.35 wt. %, or about 0.4 wt. % to any of about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, or about 10 wt. %, based on total weight of the topical composition.

In certain embodiments, the topical composition includes an effective amount of polyphenol isolates, derived from green tea with potent antioxidant properties, to assist in minimizing free-radical induced skin damage. Suitable green tea polyphenols include, but are not limited to, catechins, such as epigallocatechin gallate (EGCG), epigallocatechin (EGC), epicatechin gallate (ECG), and epicatechin (EC), cis and trans isomers thereof, salts thereof, equivalent derivatives thereof, and combinations thereof.

In certain embodiments, the topical composition includes an antioxidant system which includes any of the green tea polyphenols described herein in combination with at least one additional antioxidants.

In one embodiment, the additional antioxidants in the antioxidant system may be selected from the group of cinnamic acid, ferulic acid, caffeic acid, p-coumaric acid, sinapinic acid, cis and trans isomers thereof, salts thereof, equivalent derivatives thereof, and combinations thereof. In another embodiment, the additional antioxidants in the antioxidant system (and in the topical composition generally) may be free or substantially free of cinnamic acid, ferulic acid, caffeic acid, p-coumaric acid, sinapinic acid, cis and trans isomers thereof, salts thereof, equivalent derivatives thereof, and combinations thereof.

In certain embodiments, the additional antioxidants in the antioxidant system may be selected from the group of gallic acid, delphinidin, luteolin, quercetin, cyanidin, taxifolin, kaempferol, malvidin, hesperidin, pelargonidin, apigenin, naringenin, chrysin, ergothioneine, glutathione, emblica, cis and trans isomers thereof, salts thereof, equivalent derivatives thereof, and combinations thereof.

In certain embodiments, the additional antioxidants in the antioxidant system may be selected from the group of apigenin, ergothioneine, glutathione, emblica, cis and trans isomers thereof, salts thereof, equivalent derivatives thereof, and combinations thereof.

Each of the antioxidants in the antioxidant system may be present, individually or cumulatively, in a concentration of from any of above 0 wt. %, about 0.01 wt. %, about 0.05 wt. %, about 0.1 wt. %, about 0.15 wt. %, about 0.2 wt. %, about 0.25 wt. %, about 0.3 wt. %, about 0.35 wt. %, or about 0.4 wt. % to any of about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, or about 10 wt. %, based on total weight of the topical composition.

In certain embodiments, the antioxidant system includes apigenin that is present in the topical composition in an amount ranging from above 0 wt. % to about 0.5 wt. %, from above 0 wt. % to about 0.1 wt. %, or from above 0 wt. % to about 0.01 wt. %, based on total weight of the topical composition.

In certain embodiments, the antioxidant system includes ergothioneine that is present in the topical composition in an amount ranging from above 0 wt. % to about 0.5 wt. %, from above 0 wt. % to about 0.1 wt. %, or from above 0 wt. % to about 0.01 wt. %, based on total weight of the topical composition.

In certain embodiments, the antioxidant system includes green tea polyphenols in an amount ranging from above 0 wt. % to about 0.5 wt. %, from above 0 wt. % to about 0.1 wt. %, or from above 0 wt. % to about 0.01 wt. %, based on total weight of the topical composition.

In certain embodiments, the antioxidant system includes, comprises, consists, or consists essentially of a combination of any of the green tea polyphenols described herein and at least one of apigenin and ergothioneine in an (individual or cumulative) concentration of from any of above 0 wt. %, about 0.01 wt. %, about 0.05 wt. %, about 0.1 wt. %, about 0.15 wt. %, about 0.2 wt. %, about 0.25 wt. %, about 0.3 wt. %, about 0.35 wt. %, or about 0.4 wt. % to any of about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 3 wt. %, about 4 wt. %, about 5 wt. %, about 6 wt. %, about 7 wt. %, about 8 wt. %, about 9 wt. %, or about 10 wt. %, based on total weight of the topical composition.

In certain embodiments, the weight to weight ratio of the green tea polyphenols to the one or more additional antioxidants (individually or cumulatively) ranges from about 10:1 to about 1:10, about 8:1 to about 1:8, about 5:1 to about 1:5, about 3:1 to about 1:3, about 2:1 to about 1:2, or about 1:1.

In certain embodiments, the topical composition further includes a cosmetically acceptable excipient. Exemplary cosmetically acceptable excipients, include, without limitations, epidermal penetration enhancer, solvent, mild surfactants, oil bodies, emulsifiers, pearlescent waxes, consistency regulators, thickeners, rheology modifiers, suspending agents, chelating agents, preservatives, super fatting agents, stabilizers, polymers, silicone or siloxane compounds, fats, waxes, lecithins, phospholipids, UV photoprotective factors, biogenic active ingredients, additional antioxidants, deodorants, antiperspirants, antidandruff agents, film formers, swelling agents, insect repellents, self-tanning agents, tyrosinase inhibitors, hydrotropes, solubilizers, perfume oils, dyes, zinc oxide, fatty alcohols, esters of fatty acids, adjuvants, Natural or Synthetic Triglycerides Including Glyceryl Esters and Derivatives, hydrocarbon oils, super-fatting agents, polymers, biogenic active ingredients, hydrotropic agents, bacteria-inhibiting agents, colorants, UV screening agents, agents that absorb UV light and provide photo protection to the skin, or combinations thereof. In certain embodiments, the topical composition includes a cosmetically acceptable excipient selected from the group of solvents, emulsifiers, consistency regulators, thickeners, suspending agents, additional antioxidants, preservatives, perfume oils, or a combination thereof. In certain embodiments, the topical composition is free or substantially free of silicone compounds.

Suitable solvents that may be used in the topical compositions described herein include, without limitations, polysorbate 20, water, alkanediols (e.g., ethylene glycol, propylene glycol, butylene glycol), ethoxylated or propoxylated diglycol, ethanol, propanol, isopropanol, glycerin, methoxyisopropanol, PPG-2 methyl ether, PPG-3 methyl ether, propylene glycol butyl ether, PPG-2 butyl ether, phenoxyisopropanol, butoxyethanol, butoxydiglycol, methoxydiglycol, phenoxyethanol, PPG-3 butyl ether, PPG-2 propyl ether, propylene glycol propyl ether, or dipropylene glycol dimethyl ether, or mixtures and combinations or individual ethoxylates, propoxylates and glyceryl esters thereof.

In certain embodiments, the solvent includes, comprises, consists, or consists essentially of an alkane diol (such as ethylene glycol, propylene glycol, butylene glycol), glycerin, water, or a mixture thereof. In one embodiment, the solvent includes, comprises, consists, or consists essentially of glycerin, propylene glycol, isopentyl diol, and water.

In some embodiments, each solvent individually or all solvents together may be present in the topical composition at a concentration ranging from any of about 0.5 wt. %, about 1 wt. %, about 5 wt. %, about 10 wt. %, about 12 wt. %, about 15 wt. %, about 18 wt. %, about 20 wt. %, about 23 wt. %, or about 25 wt. % to any of about 28 wt. %, about 30 wt. %, about 35 wt. %, about 40 wt. %, about 45 wt. %, about 50 wt. %, about 55 wt. %, about 60 wt. %, about 65 wt. %, about 70 wt. %, about 75 wt. %, or about 95 wt. %, based on total weight of the topical composition. In certain embodiments, the concentration of all solvents, excluding water, in the topical composition ranges from any of about 0.5 wt. %, about 1 wt. %, about 5 wt. %, about 10 wt. %, about 12 wt. %, about 15 wt. %, about 18 wt. %, about 20 wt. %, about 23 wt. %, or about 25 wt. % to any of about 28 wt. %, about 30 wt. %, about 35 wt. %, about 40 wt. %, about 45 wt. %, or about 50 wt. %, based on total weight of the topical composition.

In certain embodiments, the cosmetically acceptable excipient includes an alkanediol (e.g., propylene glycol which may also be referred to as propanediol) that is present in the topical composition in an amount of from about 2 wt. % to about 25 wt. %, from about 5 wt. % to about 15 wt. %, or from about 8 wt. % to about 12 wt. %, based on total weight of the topical composition.

In certain embodiments, the cosmetically acceptable excipient includes glycerin in the topical composition in an amount of from about 2 wt. % to about 25 wt. %, from about 5 wt. % to about 15 wt. %, or from about 8 wt. % to about 12 wt. %, based on total weight of the topical composition.

In certain embodiments, the cosmetically acceptable excipient includes water in the topical composition in an amount of from about 5 wt. % to about 95 wt. %, about 10 wt. % to about 95 wt. %, about 20 wt. % to about 80 wt. %, from about 35 wt. % to about 70 wt. %, or from about 50 wt. % to about 60 wt. %, based on total weight of the topical composition.

In certain embodiments, the cosmetically acceptable excipient includes natural gums (e.g., a natural plant gum). Suitable natural gums include, without limitations, guar gum, carob gum, konjac gum, xanthan gum, sclerotium gum, acacia gum, cellulose gum (modified or not), or a combination thereof. In one embodiment, the natural gum in the topical composition is sclerotium gum. The natural gum contributes to the texture of the topical composition and may also act as a suspending agent for the oily phase in the aqueous phase of the emulsion.

In certain embodiments, the cosmetically acceptable excipient includes the natural gum in the topical composition in an amount of from above 0 wt. % to about 5 wt. %, from about 0.1 wt. % to about 2 wt. %, or from about 0.2 wt. % to about 0.8 wt. %, based on total weight of the topical composition.

In certain embodiments, the cosmetically acceptable excipient includes an emulsifier. Suitable emulsifiers include, without limitations, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, lsosteareth-20, Ceteareth-20, Oleth-20, Steareth-20, Steareth-21, Ceteth-20, lsoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate, or a combination thereof.

Further suitable emulsifiers are phosphate esters and the salts thereof such as cetyl phosphate (Amphisol® A), diethanolamine cetyl phosphate (Amphisol® DEA), potassium cetyl phosphate (Amphisol® K), sodium cetearyl sulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobutene. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

In certain embodiments, the cosmetically acceptable excipient includes the emulsifier in the topical composition in an amount of above 0 wt. % to about 5 wt. %, from about 0.1 wt. % to about 2 wt. %, or from about 0.2 wt. % to about 0.8 wt. %, based on total weight of the topical composition. In one embodiment, the cosmetically acceptable excipient includes an emulsifier that is PEG-7 Olivate in the topical composition in an amount of above 0 wt. % to about 5 wt. %, from about 0.1 wt. % to about 2 wt. %, or from about 0.2 wt. % to about 0.8 wt. %, based on total weight of the topical composition.

In certain embodiments, the cosmetically acceptable excipient includes a chelating agent. Suitable chelating agents include, without limitations, disodium ethylenediaminetetraacetic acid (EDTA), diethylenetriaminepentaacetic acid (DTPA), N-(hydroxyethyl)-ethylenediaminetriacetic acid (HEDTA), and nitrilotriacetic acid (NTA).

In certain embodiments, the cosmetically acceptable excipient includes the chelating agent in the topical composition in an amount of from above 0 wt. % to about 5 wt. %, from about 0.01 wt. % to about 0.5 wt. %, or from about 0.05 wt. % to about 0.3 wt. %, based on total weight of the topical composition. In one embodiment, the cosmetically acceptable excipient includes a chelating agent that is EDTA in the topical composition in an amount of from above 0 wt. % to about 5 wt. %, from about 0.01 wt. % to about 0.5 wt. %, or from about 0.05 wt. % to about 0.3 wt. %, based on total weight of the topical composition.

In certain embodiments, the cosmetically acceptable excipient includes additional antioxidants such as a form of Vitamin E. Suitable forms of Vitamin E that may be included in the topical composition can be selected from alpha, beta, delta, and gamma tocopherols, and alpha, beta, delta and gamma tocotrienols, and combinations thereof.

In certain embodiments, any combination of any of the forms of Vitamin E may be present (individually or cumulatively) in the topical composition in an amount of from about 0.1 wt. % to about 5 wt. %, from about 0.3 wt. % to about 3 wt. %, or from about 0.5 wt. % to about 2 wt. %, based on total weight of the topical composition.

In certain embodiments, the cosmetically acceptable excipient in the topical composition includes a preservative. Suitable preservative agents include, for example, phenoxyethanol, a solution of paraben, pentanediol and sorbic acid, as well as silver complexes which are known under the commercial reference Surfacine® and other classes of substances set out in annex 6, parts A and B of the cosmetic regulations, i.e. a suitable preservative.

In certain embodiments, the cosmetically acceptable excipient includes a preservative in an amount of above 0 to about 5 wt. %, from about 0.3 wt. % to about 3 wt. %, or from about 0.5 wt. % to about 2 wt. %, based on total weight of the topical composition. In certain embodiments, the cosmetically acceptable excipient includes a preservative that is phenoxyethanol in an amount of above 0 to about 5 wt. %, from about 0.3 wt. % to about 3 wt. %, or from about 0.5 wt. % to about 2 wt. %, based on total weight of the topical composition.

In certain embodiments, the cosmetically acceptable excipient includes a perfume oil. Suitable perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

Essential oils of relatively low volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, galbanum oil, labolanum oil and lavandin oil. Other suitable oils include bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

In certain embodiments, the cosmetically acceptable excipient includes a perfume oil that is an essential oil selected from the group of a lavender oil, a bergamot oil, a eucalyptus oil, a chamomile oil, a melaleuca oil, or a combination thereof. In one embodiment, the cosmetically acceptable excipient includes a lavender oil, a chamomile oil, or a combination thereof.

In certain embodiments, the perfume oil (each perfume oil individually or all perfume oils in the topical composition cumulatively) is present in the topical composition an amount of above 0 wt. % to about 5 wt. %, from above 0 wt. % to about 1 wt. %, or from about 0.01 wt. % to about 0.3 wt. %, based on total weight of the topical composition.

In certain embodiments, the pH of the topical composition ranges from any of about 2.0, about 2.1, about 2.2, about 2.3, about 2.4, about 2.5, about 2.6, about 2.7, about 2.8, about 2.8, or about 2.9 to any of about 3.0, about 3.1, about 3.2, about 3.3, about 3.4, about 3.5, about 3.6, about 3.7, about 3.8, about 3.8, about 3.9, or about 4.0. In certain embodiments, the pH of the topical composition is about 2.0 to about 4.0, about 2.5 to about 3.5, or about 2.7 to about 3.3.

In certain embodiments, the topical compositions described herein is lightweight formulation that includes fast absorbing constituents and/or constituents that diffuse into the skin over time. In certain embodiments, the formulation provides one or more of moisturization of the skin, environmental protection, brightening of complexion, and anti-aging benefits. In certain embodiments, the texture of the topical composition is one or more of smooth, silky, soft, and non-oily.

The topical compositions described herein may be formulated in any dermatological acceptable vehicle such as a serum, emulsion, cream, foam, spray, ointment, gel, lotion, or as a pad or roll-on applied formulation, which may contain ingredients to improve, modify, or stabilize the composition physically or cosmetically.

The topical compositions according to the disclosure may also contain one or one more additional cosmetically acceptable excipients as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerization of unsaturated fatty alcohols).

Examples of such ester oils are isopropyl myristate, isopropyl palmitate, isopropyl stearate, isopropyl isostearate, isopropyl oleate, n-butyl stearate, n-hexyl laurate, n-decyl oleate, isooctyl stearate, iso-nonylstearate, isononyl isononanoate, 2-ethylhexylpalmitate, 2-hexyllaurate, 2-hexyldecyl stearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants

Diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

Natural or Synthetic Triglycerides Including Glyceryl Esters and Derivatives

Di- or triglycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borage oil, etc.

Waxes including esters of long-chain acids and alcohols as well as compounds having wax-like properties, e.g., carnauba wax, beeswax (white or yellow), lanolin wax, candelilla wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethylene glycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycol ether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropyene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropyl ene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkyl betaine, N-alkylaminobetaines. Alkylimidazolines, alkylopeptides, lipoaminoacides, self-emulsifying bases and the compounds as described in K. F. DePolo, A short textbook of cosmetology, Chapter 8, Table 8-7, p 250-251.

Nonionic bases such as PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and polysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Anionic alkaline bases such as PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

Adjuvants and Additives

The cosmetic sunscreen compositions, for example creams, gels, lotions, alcoholic and aqueous/alcoholic solutions, emulsions, wax/fat compositions, stick preparations, powders or ointments, may in addition contain, as further adjuvants and additives such as, mild surfactants, super-fatting agents, consistency regulators, thickeners, polymers, stabilizers, biogenic active ingredients, swelling agents, further UV light-protective factors, antioxidants, hydrotropic agents, preservatives, self-tanning agents, solubilizers, perfume oils, colorants, bacteria-inhibiting agents and the like.

Super-Fatting Agents

Substances suitable for use as super-fatting agents are, for example, lanolin and lecithin and also polyethoxylated or acetylated lanolin and lecithin derivatives, polyol fatty acid esters, monoglycerides and fatty acid alkanolamides, the latter simultaneously acting as foam stabilizers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carrageenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacrylamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/C10-30 alkyl acrylate crosspolymer), LUVIGEL EM (sodium acrylates copolymer), ACULYN 28 (acrylates/beheneth-25 methacrylate copolymer), etc.

Polymers

As anionic, zwitterionic, amphoteric and non-ionic polymers come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore, the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, deoxyribonucleic acid, retinol, bisabolol, allantoin, phytantriol, panthenol, AHA acids, amino acids, ceramides, pseudoceramides, essential oils, plant extracts and vitamin complexes.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Hydrotropic Agents

To improve the flow behaviour, it is also possible to employ hydrotropic agents, for example ethoxylated or non-ethoxylated mono-alcohols, diols or polyols with a low number of carbon atoms or their ethers (e.g. ethanol, isopropanol, 1,2-dipropanediol, propylene glycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo-A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent.

Colorants

There may be used as colorants the substances that are suitable and permitted for cosmetic purposes, as compiled, for example, in the publication "Kosmetische Farbemittel" of the Farbstoffkommission der Deutschen Forschungsgemeinschaft, Verlag Chemie, Weinheim, 1984, pages 81 to 106.

UV Screening Agents

Suitable sun screening agents would include a range of organic UV screening agents selected from the group consisting of 1(+/−)-1,7,7-trimethyl-3-[(4-methylphenyl)methylene]bicyclo-[2.2.1]heptan-2-one; p-methyl benzylidene camphor, 1,7,7-trimethyl-3-(phenylmethylene)bicyclo[2.2.1]heptan-2-one; benzylidene camphor, (2-Hydroxy-4-methoxyphenyl)(4-methylphenyl)methanone, 2,4-dihydroxybenzophenone, 2,2',4,4'-tetrahydroxybenzophenone, 2-Hydroxy-4-methoxy benzophenone, 2-Hydroxy-4-methoxy benzophenone-5-sulfonic acid, 2,2'-dihydroxy-4,4'-dimethoxybenzophenone, 2,2'-Dihydroxy-4-methoxybenzophenone, Alpha-(2-oxoborn-3-ylidene)toluene-4-sulphonic acid and its salts, 1-[4-(1,1-dimethylethyl)phenyl]-3-(4-methoxyphenyl)propane-1,3-dione, Methyl N,N,N-trimethyl-4-[(4,7,7-trimethyl-3-oxobicyclo[2,2,1]-hept-2-ylidene)methyl]anilinium sulphate, 3,3,5-Trimethyl cyclohexyl-2-hydroxy benzoate, Isopentyl p-methoxycinnamate, Menthyl-o-aminobenzoate, 2-Ethylhexyl 2-cyano-3,3-diphenylacrylate, 2-ethylhexyl 4-(dimethylamino)benzoate, 2-ethylhexyl 4-methoxycinnamate, 2-ethylhexyl salicylate, Benzoic acid, 4,4',4"-(1,3,5-triazine-2,4,6-triyltriimino)tris-,tris(2-ethylhexyl)ester, 4-aminobenzoic acid, Benzoic acid, 4-amino-, ethyl ester, polymer with oxirane, 2-phenyl-1H-benzimidazole-5-sulphonic acid, 2-Propenamide, N-[[4-[(4,7,7-trimethyl-3-oxobicyclo[2.2.1]hept-2-ylidene)methyl]phenyl]methyl]-, homopolymer. Triethanolamine salicylate, 3,3'-(1,4-phenylenedimethylene)bis[7,7-dimethyl-2-oxo-bicyclo[2.2.1]heptane-1 methanesulfonic acid], Titanium dioxide, 2,2'-Methylene-bis-[6-(2H-benzotriazol-2-yl)-4-(1,1,3,3-tetramethylbutyl)-phenol], Bis-Ethylhexyloxyphenol Methoxyphenyl Triazine, 1H-Benzimidazole-4,6-disulfonic acid, 2,2'-(1,4-phenylene)bis-, disodium salt, Benzoic acid, 4,4'-[[6-[[4-[[(1,1-dimethylethyl)amino]carbonyl]-phenyl]amino]1,3,5-triazine-2,4-diyl]diimino] bis-, Phenol, 2-(2H-benzotriazol-2-yl)-4-methyl-6-[2-methyl-3-[1,3,3,3-tetramethyl-1-[(trimethylsily)oxy] disiloxanyl]propyl]-, Dimethicodiethylbenzalmalonate, Benzenesulfonic acid, 3-(2H-benzotriazol-2-yl)-4-hydroxy-5-(1-methyl propyl)-, monosodium salt, Benzoic acid, 2-[4-(diethylamino)-2-hydroxybenzoyl]-, hexyl ester, 1-Dodecanaminium, N-[3-[[4-(dimethylamino)benzoyl]amino]-propyl] N,N-dimethyl-, salt with 4-methylbenzenesulfonic acid (1:1), 1-Propanaminium, N,N,N-trimethyl-3-[(1-oxo-3-phenyl-2-propenyl) amino]-, chloride, 1H-Benzimidazole-4,6-disulfonic acid, 2,2'-(1,4-phenylene)bis-, 1,3,5-Triazine, 2,4,6-tris(4-methoxyphenyl)-1,3,5-Triazine, 2,4,6-tris[4-[(2-ethylhexyl)oxy]phenyl]-, 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt), 2-Propenoic acid, 3-(1H-imidazol-4-yl)-, Benzoic acid, 2-hydroxy-, [4-(1-methylethyl)phenyl] methyl ester, 1,2,3-Propanetriol, 1-(4-aminobenzoate), Benzeneacetic acid, 3,4-dimethoxy-a-oxo-, 2-Propenoic acid, 2-cyano-3,3-diphenyl-, ethyl ester, Anthralinic acid, p-menth-3-yl ester, 2,2'-bis(1,4-phenylene)-1H-benzimidazole-4,6-disulphonic acid mono sodium salt or Disodium phenyl dibenzimidazole tetrasulfonate, 1,3,5-Triazine-2,4,6-triamine and N,N'-bis[4-[5-(1,1-dimethylpropyl)-2-benzoxazolyl]phenyl]-N''-(2-ethylhexyl).

Agents that Absorb UV Light and Provide Photo Protection to the Skin

Suitable agents that absorb UV light, provide photo protection to the skin, and optionally provide sunless tanning may include a compound of formula I:

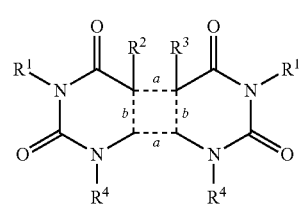

wherein:
each $R^1$ is independently H, $(C_1-C_6)$alkyl, $(C_3-C_7)$carbocycle or $R_aC(=O)—$, and the two $R^4$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or
each $R^4$ is independently H, $(C_1-C_6)$alkyl, $(C_3-C_7)$carbocycle or $R_aC(=O)—$, and the two $R^1$ groups together form a $—(C_3-C_8)$alkyl-group, a $—(C_2-C_6)$alkyl-Y—$(C_2-C_6)$alkyl-group or a $—(C_1-C_6)$alkyl-Y'—$(C_1-C_6)$alkyl-group; or the two $R^4$ groups together form a —$(C_3$-$C_8)$alkyl-group, a —$(C_2$-$C_6)$alkyl-Y—$(C_2$-$C_6)$alkyl group or a —$(C_1$-$C_6)$alkyl-Y'—$(C_1$-$C_6)$alkyl-group and the two $R^1$ groups together form a —$(C_3$-$C_8)$alkyl-group, a —$(C_2$-$C_6)$alkyl-Y—$(C_2$-$C_6)$alkyl-group or a —$(C_1$-$C_6)$alkyl-Y'—$(C_1$-$C_6)$alkyl-group;

the dashed bonds labeled "a" are absent and the dashed bonds labeled "b" are double bonds; or all the dashed bonds are single bonds;

$R^2$ is H, $(C_1$-$C_6)$alkyl or aryl, wherein aryl is optionally substituted with one or more $Z^1$ groups;

$R^3$ is H, $(C_1$-$C_6)$alkyl or aryl, wherein aryl is optionally substituted with one or more $Z^1$ groups;

Y is O, S, NH, $NR_c$, P, P($=$O) or POH;

Y' is $Si(R_b)_2$ or —$Si(R_b)_2$—O—$Si(R_b)_2$—;

each $R_a$ is independently $(C_1$-$C_6)$alkyl, $(C_3$-$C_7)$carbocycle or aryl, wherein aryl is optionally substituted with one or more $Z^1$ groups;

each $R_b$ is independently $(C_1$-$C_6)$alkyl, $(C_3$-$C_7)$carbocycle or aryl, wherein aryl is optionally substituted with one or more $Z^1$ groups;

each $R_c$ is independently $R_g$ or a $C_1$-$C_{18}$ saturated or unsaturated carbon chain that is optionally substituted with one or more groups independently selected from oxo ($=$O), hydroxy, mercapto, $(C_1$-$C_6)$alkoxy, $(C_1$-$C_6)$alkoxycarbonyl, $(C_1$-$C_6)$alkanoyloxy, $NR_dR_e$, carboxy, and aryl, wherein any aryl of $R_c$ is optionally substituted with one or more $R_f$;

each $R_d$ and $R_e$ is independently selected from H, $(C_1$-$C_6)$alkyl, $(C_1$-$C_6)$alkanoyl, phenyl, benzyl, and $R_g$;

each $R_f$ is independently selected from $(C_1$-$C_6)$alkyl, $(C_1$-$C_6)$alkoxy, $(C_1$-$C_6)$alkoxycarbonyl, $(C_1$-$C_6)$alkanoyloxy, —C($=$O)-phenyl, and —C($=$O)CH$_2$C($=$O)-phenyl, wherein any phenyl is optionally substituted with one or more groups independently selected from $(C_1$-$C_6)$alkyl, —SO$_3$H, and $(C_1$-$C_6)$alkoxy;

each $R_g$ is

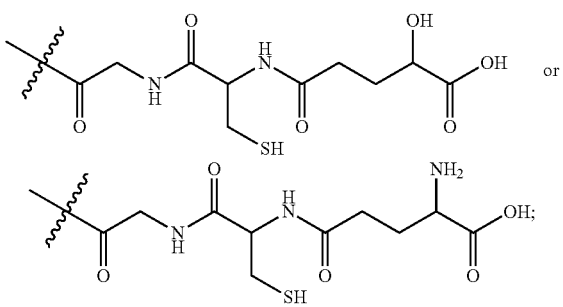

each $Z^1$ is independently selected from $(C_1$-$C_6)$alkyl, halogen, —CN, —$OR_{n1}$, —$NR_{q1}R_{r1}$, —$NR_{n1}COR_{p1}$, —$NR_{n1}CO_2R_{p1}$, NO$_2$, —C(O)$R_{n1}$, —C(O)O$R_{n1}$ and —C(O)$NR_{q1}R_{r1}$, wherein any $(C_1$-$C_6)$alkyl of $Z^1$ is optionally substituted with one or more (e.g. 1, 2, 3, 4, 5 or 6) halogen;

each $R_{n1}$ is independently selected from H and $(C_1$-$C_6)$alkyl, wherein any $(C_1$-$C_6)$alkyl of $R_{n1}$ is optionally substituted with one or more (e.g. 1, 2, 3, 4, 5 or 6) halogen;

each $R_{p1}$ is independently $(C_1$-$C_6)$alkyl; and $R_{q1}$ and $R_{r1}$ are each independently selected from H and $(C_1$-$C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine; or a salt thereof.

Specific groups of compounds and specific compounds of Formula I that may be incorporated in the topical composition described herein and methods of preparing such compounds are described in U.S. Pat. No. 9,403,778 and in U.S. Pat. No. 9,987,211, which are incorporated herein by reference in its entirety.

Suitable agents that absorb UV light, provide photo protection to the skin, and optionally provide sunless tanning may include a compound of formula II:

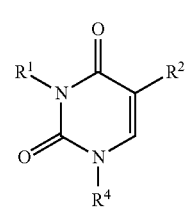

II or a salt thereof, wherein:

$R^1$ is H, $(C_1$-$C_6)$alkyl, $(C_3$-$C_7)$carbocycle or $R_aC(=O)$—;

$R^2$ is H, $(C_1$-$C_6)$alkyl or aryl, wherein aryl is optionally substituted with one or more (e.g. 1, 2, 3, 4 or 5) $Z^1$ groups;

$R^4$ is H, $(C_1$-$C_{10})$alkyl, $(C_3$-$C_7)$carbocycle or $R_aC(=O)$—;

$R_a$ is or $(C_1$-$C_6)$alkyl, $(C_3$-$C_7)$carbocycle or aryl, wherein aryl is optionally substituted with one or more (e.g. 1, 2, 3, 4 or 5) $Z^1$ groups;

each $Z^1$ is independently selected from $(C_1$-$C_6)$alkyl, halogen, —CN, —$OR_{n1}$, —$NR_{q1}R_{r1}$, —$NR_{n1}COR_{p1}$, —$NR_{n1}CO_2R_{p1}$, NO$_2$, —C(O)$R_{n1}$, —C(O)O$R_{n1}$ and —C(O)$NR_{q1}R_{r1}$, wherein any $(C_1$-$C_6)$alkyl of $Z^1$ is optionally substituted with one or more (e.g. 1, 2, 3, 4, 5 or 6) halogen;

each $R_{n1}$ is independently selected from H and $(C_1$-$C_6)$alkyl, wherein any $(C_1$-$C_6)$alkyl of $R_{n1}$ is optionally substituted with one or more (e.g. 1, 2, 3, 4, 5 or 6) halogen;

each $R_{p1}$ is independently $(C_1$-$C_6)$alkyl; and $R_{q1}$ and $R_{r1}$ are each independently selected from H and $(C_1$-$C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine.

Specific groups of compounds and specific compounds of Formula II that may be incorporated in the topical composition described herein and methods of preparing such compounds are described in U.S. Pat. No. 9,987,211, which is incorporated herein by reference in its entirety.

Suitable agents that absorb UV light and provide photo protection to the skin may include a compound of formula III:

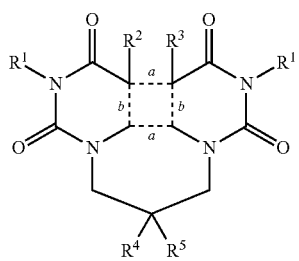

wherein:
  each $R^1$ is independently H, $(C_1-C_6)$alkyl, $(C_3-C_7)$carbocycle or $R_aC(=O)$; or the two $R^1$ groups together form a $-(C_3-C_8)$alkyl-group, a $-(C_2-C_6)$alkyl-Y$-(C_2-C_6)$alkyl-group or a $-(C_1-C_6)$alkyl-Y'$-(C_1-C_6)$alkyl-group; or
  the dashed bonds labeled "a" are absent and the dashed bonds labeled "b" are double bonds; or all the dashed bonds are single bonds;
  $R^2$ is H, $(C_1-C_6)$alkyl or aryl, wherein aryl is optionally substituted with one or more (e.g. 1, 2, 3, 4 or 5) $Z^1$ groups;
  $R^3$ is H, $(C_1-C_6)$alkyl or aryl, wherein aryl is optionally substituted with one or more (e.g. 1, 2, 3, 4 or 5) $Z^1$ groups;
  $R^4$ is hydroxy, carboxy, $(C_1-C_6)$alkoxycarbonyl, $-OPO_3H_2$, $-OR_c$, or $-NR_dR_e$; and $R^5$ is H; or $R^4$ and $R^5$ taken together are oxo;
  Y is O, S, NH, P, P(=O) or POH;
  Y' is $Si(R_b)_2$ or $-Si(R_b)_2-O-Si(R_b)_2-$;
  each $R_a$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;
  each $R_b$ is independently $(C_1-C_6)$alkyl, $(C_3-C_7)$carbocycle or aryl, wherein aryl is optionally substituted with one or more (e.g. 1, 2, 3, 4 or 5) $Z^1$ groups;
  $R_c$ is $R_f$ or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;
  $R_d$ is H, $(C_1-C_6)$alkyl, or $(C_1-C_6)$alkanoyl;
  $R_e$ is H or a $C_1-C_{20}$ saturated or $C_2-C_{20}$ unsaturated carbon chain that is optionally substituted with one or more groups independently selected from oxo (=O), hydroxy, mercapto, $(C_1-C_6)$alkoxy, $(C_1-C_6)$alkoxycarbonyl, $(C_1-C_6)$alkanoyloxy, $NR_dR_e$, carboxy, and aryl, wherein aryl is optionally substituted with one or more (e.g. 1, 2, 3, 4 or 5) $Z^1$ groups;
  each $R_f$ is:

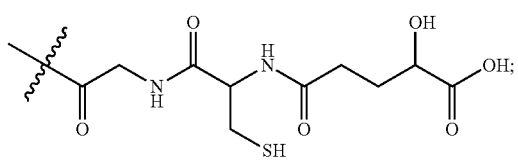 [SMILES: *C(=O)CNC(=O)C(CS)NC(=O)CCC(O)C(=O)O]

each $Z^1$ is independently selected from $(C_1-C_6)$alkyl, halogen, $-CN$, $-OR_{n1}$, $-NR_{q1}R_{r1}$, $-NR_{n1}COR_{p1}$, $-NR_{n1}CO_2R_{p1}$, $NO_2$, $-C(O)R_{n1}$, $-C(O)OR_{n1}$ and $-C(O)NR_{q1}R_{r1}$, wherein any $(C_1-C_6)$alkyl of $Z^1$ is optionally substituted with one or more (e.g. 1, 2, 3, 4, 5 or 6) halogen;
  each $R_{n1}$ is independently selected from H and $(C_1-C_6)$alkyl, wherein any $(C_1-C_6)$alkyl of $R_{n1}$ is optionally substituted with one or more (e.g. 1, 2, 3, 4, 5 or 6) halogen;
  each $R_{p1}$ is independently $(C_1-C_6)$alkyl; and
  $R_{q1}$ and $R_{r1}$ are each independently selected from H and $(C_1-C_6)$alkyl or $R_{q1}$ and $R_{r1}$ together with the nitrogen to which they are attached form a piperidine, pyrrolidine, morpholine, azetidine, thiomorpholine, piperazine or 4-methylpiperazine;
or a salt thereof.

Specific groups of compounds and specific compounds of Formula III that may be incorporated in the topical composition described herein and methods of preparing such compounds are described in U.S. Pat. No. 9,364,406 and in U.S. Pat. No. 9,987,211, which are incorporated herein by reference in its entirety.

Sunscreening Agents

Topical Compositions disclosed herein may include sun screening agents such as avobenzone, ecamsule, methyl anthranilate, oxybenzone, dioxybenzone, sulisobenzone, octinoxate, homosalate, octocrylene and octisalate. Such compositions may comprise organic UV filters, so-called hydrophilic or lipophilic sun-protection filters, which are effective in the UVA region and/or UVB region and (/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the WO93/04665. Further examples of organic filters are indicated in patent application EP-A 0 487 404. Particularly suitable for a combination are: para-aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed under the name "Uvinul P25" by BASF.

Other UV filter ingredients which may be incorporated in the topical compositions of the disclosure include:

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, Octocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed by Chimex under the name "Mexoryl SD", 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronized form as an aqueous dispersion, for example marketed by BASF under the name "Tinosorb M".

Triazine derivatives: ethylhexyltriazone, for example marketed under the name "Uvinul T150" by BASF, diethylhexylbutamidotriazone, for example marketed under the name "Uvasorb HEB" by Sigma 3V, 2,4,6-tris(diisobutyl 4'-aminobenzalmalonate)-s-triazine or 2,4,6-tris(biphenyl)-1,3,5-triazine. marketed as Tinosorb A2B by BASF, 2,2'-[6-(4-methoxyphenyl)-1,3,5-triazine-2,4-diyl]bis[5-(2-ethylhexyl)oxy]phenol, marketed as Tinosorb S by BASF, N2,N4-bis[4-[5-(1,1-dimethylpropyl)-2-benzoxazolyl]phenyl]-N-6-(2-ethylhexyl)-1,3,5-triazine-2,4,6-triamine marketed as Uvasorb K 2A by Sigma 3V.

Anthraniline derivatives: Menthyl anthranilate, for example marketed by Symrise under the name "Neo Heliopan MA".

Imidazole derivatives: Ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1, 1-Dicarboxy(2,2'-dimethylpropyl)-4,4-diphenylbutadiene.

Benzoxazole derivatives: 2,4-bis[5-(l-dimethylpropyl)benzoxazol-2-yl(4-phenyl) imino]-6-(2-ethylhexyl)imino-1,3,5-triazine, for example marketed by Sigma 3V under the name Uvasorb K2A, and mixtures comprising this.

Suitable organic UV-protecting substances can preferably be selected from: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15,1,1-Dicarboxy(2,2'-dimethylpropyl)-4,4-diphenylbutadiene, 2,4-bis[5-1(dimethylpropyl)benzoxazol-2-yl(4-phenyl) imino]-6-(2-ethylhexyl)imino-1,3,5-triazine and mixtures thereof.

The compositions of the invention may comprise further inorganic UV filters, so-called particulate UV filters. These combinations with particulate UV filters are possible both as powder and also as dispersion or paste. In an embodiment the inorganic UV filter is a titanium dioxide, such as, for example, coated titanium dioxide (for example Eusolex® T-2000, Eusolex® T-AQUA, Eusolex® T-AVO, Eusolex® T-OLEO), a zinc oxide (for example Sachtotec), an iron oxide or a cerium oxide and/or zirconium oxide. Furthermore, combinations with pigmentary titanium dioxide or zinc oxide are also possible, where the particle size of these pigments are greater than or equal to 200 nm, for example Hombitan® FG or Hombitan® FFPharma.

Compositions of the invention may comprise inorganic UV filters which have been after treated by conventional methods, as described, for example, in *Cosmetics & Toiletries,* 1990, 105, 53-64. One or more of the following aftertreatment components can be: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

In an embodiment, particulate UV filters used in compositions of the invention are:

untreated titanium dioxides, such as, the products Microtitanium Dioxide MT 500 B from Tayca; titanium dioxide P25 from Degussa, after treated micronized titanium dioxides with aluminium oxide and silicon dioxide aftertreatment, such as, the product "Microtitanium Dioxide MT 100 SA from Tayca; or the product "Tioveil Fin" from Uniqema, after treated micronized titanium dioxides with aluminium oxide and/or aluminium stearate/laurate aftertreatment, such as, Microtitanium Dioxide MT 100 T from Tayca, Eusolex T-2000 from Merck, after treated micronized titanium dioxides with iron oxide and/or iron stearate aftertreatment, such as, the product "Microtitanium Dioxide MT 100 F" from Tayca, after treated micronized titanium dioxides with silicon dioxide, aluminium oxide and silicone aftertreatment, such as, the product "Microtitanium Dioxide MT 100 SAS", from Tayca, after treated micronized titanium dioxides with sodium hexametaphosphates, such as, the product "Microtitanium Dioxide MT 150 W" from Tayca.

The treated micronized titanium dioxides employed for the combination may also be after treated with:

octyltrimethoxysilanes; such as, the product Tego Sun T 805 from Evonik Goldschmidt GmbH, silicon dioxide; such as, for example, the product Parsol T-X from DSM, aluminium oxide and stearic acid; such as, the product UV-Titan M160 from Sachtleben, aluminium and glycerin; such as, the product UV-Titan from Sachtleben, aluminium and silicone oils, such as, the product UV-Titan M262 from Sachtleben, sodium hexametaphosphate and polyvinylpyrrolidone, polydimethylsiloxanes, such as, the product 70250 Cardre UF TiO2SI3" from Cardre, polydimethylhydrogenosiloxanes, such as, for example, the product Microtitanium Dioxide USP Grade Hydrophobic" from Color Techniques.

In a particular embodiment, compositions of the invention may include untreated zinc oxides, such as, the product Z-Cote from BASF (Sunsmart), Nanox from Elementis. In another particular embodiment, compositions of the invention may include after treated zinc oxides, such as, the following products:

"Zinc Oxide CS-5" from Toshibi (ZnO after treated with polymethylhydrogeno-siloxanes);

Nanogard Zinc Oxide FN from Nanophase Technologies;

"SPD-Z1" from Shin-Etsu (ZnO after treated with a silicone-grafted acrylic polymer, dispersed in cyclodimethylsiloxanes;

"Escalol Z100" from ISP (aluminium oxide-after treated ZnO dispersed in an ethylhexyl methoxycinnamate/PVP-hexadecene/methicone copolymer mixture); and "Fuji ZNO-SMS-10" from Fuji Pigment (ZnO after treated with silicon dioxide and polymethylsilesquioxane).

In another particular embodiment, compositions of the invention may include untreated cerium oxide micropigment, for example with the name "Colloidal Cerium Oxide" from Rhone Poulenc. In another particular embodiment, compositions of the invention may include untreated and/or after treated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, mixtures of aluminium oxide, silicon dioxide and silicone-after treated titanium dioxide, zinc oxide mixtures, such as, the product UV-Titan M261 from Sachtleben, can also be used in combination with the UV protection agents according to the invention.

Methods of Use

In some embodiments, the present disclosure is directed to a method of treating a skin of a subject for effects of radical-induced damage. Radical-induced damage may encompass damage from free radicals from sunlight (UVB, UVA, Visible Light), HEV (blue) light, Infrared (IR), pollution, irritants, allergens, and various environmental toxins that are destructive to the skin, for example, by hydrolyzing elastin fibers in the skin and desynthesizing collagen in the lower dermal layers of the skin. Exemplary radical-induced damage that may be treated, prevented, minimized, reduced, or attenuated after administering to a skin of a subject an effective amount of any of the topical compositions described herein includes, without limitations, skin wrinkles, appearance of fine lines, skin roughness, skin sagging, skin firmness, reduction in skin elasticity, age spots, hyperpigmentation, scars, skin surface irregularities, rosacea, acne, psoriasis, reduction in the skin's regenerative and renewal process, weather-beaten appearance, yellowing, redness, dryness, ichthyosis, and other damaging skin conditions.

In certain embodiments, the present disclosure is directed to a method of brightening a skin of a subject by administering to the skin of a subject an effective amount of any of the topical compositions described herein, wherein the skin is brightened after administration of the topical composition.

In certain embodiments, the present disclosure is directed to a method treating a skin of a subject for effects of atmospheric or extrinsic aging by administering to the skin of a subject an effective amount of any of the topical compositions described herein, wherein the skin exhibits reduction or attenuation of effects of atmospheric or extrinsic aging after administration.

In certain embodiment, the present disclosure is directed to a treatment regimen method that includes administering to a skin of a subject that has been subjected to a dermatological procedure an effective amount of any of the topical compositions described herein. Dermatological procedure that may benefit for subsequent (i.e., post procedure) administration of the topical compositions described herein include, without limitations, non-ablative dermatological procedures, chemical peel, micro-abrasion, laser, and the like. In certain embodiments, the methods described herein further include performing the dermatological procedure after administration of the topical composition and/or before administration of the topical composition, depending on the treatment regimen. In certain embodiments, the topical compositions described herein is helpful in improving the outcomes of dermatological procedures, e.g., by speeding healing, quelling discomfort, quenching reactive oxygen species (ROS), inducing collagen formation, or any combination thereof.

As used herein, the terms "treatment" or "treating" with respect to a skin condition generally mean "having positive effect on a skin condition" and encompass reduction, amelioration, and/or alleviation of at least one symptom of a skin condition, a reduction, amelioration, and/or alleviation in the severity of the skin conditions, or delay, prevention, or inhibition of the progression of the skin condition, or the perception thereof. Treatment, as used herein, therefore does not require total curing of the condition. A formulation of the present disclosure that is useful for treatment of a skin condition, or a method of treating a skin condition, need only reduce the severity of a skin condition, reduce the severity of symptoms associated therewith, provide improvement to a patient's quality of life, or delay, prevent, or inhibit the onset of one or more symptoms of a skin condition. As used herein, these terms also encompass aesthetic improvements to the skin upon application of the disclosed formulations having a combination of, for example, an ascorbate component and green tea polyphenols.

As used herein, the phrase "effective amount" refers to an amount of a topical composition of the present disclosure, or component thereof, effective to treat a skin condition as noted above, including a range of effects, from a detectable local improvement in an area of topical application to substantial relief of symptoms to an improvement in one or more aesthetic criteria, including, but not limited to, a perceived improvement in damage from free radicals from sunlight (UVB, UVA, Visible Light), HEV (blue) light, Infrared (IR), pollution, irritants, allergens, and various environmental toxins, skin wrinkles, appearance of fine lines, skin roughness, skin sagging, skin firmness, skin elasticity, age spots, hyperpigmentation, scars, skin surface irregularities, rosacea, acne, psoriasis, skin's regenerative and renewal process, weather-beaten appearance, yellowing, redness, dryness, ichthyosis, and other damaging skin conditions.

The effective amount will vary with the particular condition or conditions being treated, the severity of the condition, the duration of the treatment, the specific components of the composition being used, and other factors. In certain embodiments, the topical compositions described herein are suitable for administration by frequent periodic application, such as by a once, twice, thrice or four times daily application or more, e.g., for a duration of at least 1 day, at least 3 days, at least 5 days, at least 7 days, at least 10 days, at least 14 days, at least 21 days, at least 30 days, and so on. Accordingly, in certain embodiments, the methods described herein further include periodically repeating the administration of the topical composition.

In certain embodiments, the topical compositions described herein are suitable for a pre or post procedure administration, such as before or after a dermatological procedure.

In certain embodiments, since the topical composition described herein is an emulsion of an aqueous and an oily phase, the two phases may separate during storage. Accordingly, in certain embodiments, the methods described herein further include shaking the topical composition to uniformly disperse the oily phase within the aqueous phase prior to administration.

Method of Preparation

The instant disclosure is also directed to a method of preparing any of the topical compositions described herein. The method includes producing any of the topical compositions described herein by combining an ascorbate component, above 0 wt. % to about 1 wt. % of an antioxidant system that includes green tea polyphenols, and a optionally at least one cosmetically acceptable excipient.

The topical composition may be formulated into a serum, gel, lotion, cream, pad applied formulation, and the like.

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

A topical composition in accordance with embodiments described herein was formulated into a serum having the composition described in Table 1 below. The serum was an emulsion of an aqueous phase and an oily phase and had a pH ranging from about 2.5 to about 3.5.

TABLE 1

Serum Composition

| Ingredient | Amount (wt. %) |
| --- | --- |
| Water | 50 wt. %-60 wt. % |
| Ascorbic Acid | 10 wt. %-30 wt. % |
| Tetrahexyldecyl Ascorbate | 2 wt. %-20 wt. % |
| Green Tea Polyphenols | Above 0 wt. %-0.5 wt. % |
| Apigenin | Above 0 wt. %-0.5 wt. % |
| Ergothioneine | Above 0 wt. %-0.5 wt. % |
| Sclerothium Gum | 0.2 wt. %-0.8 wt. % |
| Disodium EDTA | 0.05 wt. %-0.3 wt. % |
| Glycerin | 5 wt. %-15 wt. % |
| Propanediol | 5 wt. %-15 wt. % |
| Tocopheryl Acetate | 0.5 wt. %-2 wt. % |
| PEG-7 Olivate | 0.2 wt. %-0.8 wt. % |
| Lavender Essential Oil | 0.01 wt. %-0.3 wt. % |
| Chamomile Essential Oil | 0.01 wt. %-0.3 wt. % |
| Phenoxyethanol | 0.5 wt. %-2 wt. % |

Example 2

A clinical trial was conducted to assess the safety and efficacy of the topical composition including Vitamin C and E and green tea polyphenols (CE-GTP) on photoaged facial skin.

The study was conducted over 12 weeks to assess the safety and efficacy of CE-GTP serum in photoaged facial skin in 31 female subjects aged 21 to 65 years who had not had any facial treatments in the past six months. The detailed inclusion and exclusion criteria are presented in Table 2 and a summary of demographic information is presented in Table 3.

TABLE 2

Inclusion and exclusion criteria

Inclusion Criteria
Female, 21 to 65 years of age.
In good general health.
Fitzpatrick skin type I-VI.
Mild to moderate scores for the following parameters on the global face:
  Wrinkles
  Hyperpigmentation
  Firmness (visual)
No facial treatments in past 6 months and willing to withhold during study duration.
Exclusion Criteria
Diagnosed with allergies to facial skin care products.
Nursing, pregnant, or planning to become pregnant during study.
History of skin cancer within past 5 years.
Currently taking or have taken:
  Oral isotretinoin (Accutane ®) within last 6 months
  Avita ®, Differin ®, Renova ®, Retin-A ®, Retin-A Micro ®, Soriatane ®, or Tazorac ® within 3 months
  Prescription-strength skin-lightening within 3 months
  Any anti-wrinkle, skin-lightening, or other product or topical or systemic medication known to affect skin aging or dyschromia within 2 weeks
Dental surgery/procedures within 4 weeks before study start date or planning to have dental surgery/procedures during study.
Health condition and/or pre-existing dermatologic disease on the face deemed inappropriate for participation or could interfere with the outcome of the study.
Observable sunburn, suntan, scars, nevi, excessive hair, tattoos, or other dermal conditions on the face that may influence test results.
History of immunosuppression/immune deficiency, organ transplant, or currently using oral or systemic immunosuppressive medications and and/or undergoing radiation or chemotherapy.
Using or having regularly used systemic or topical corticosteroids within past 4 weeks.
Disease such as asthma, diabetes, epilepsy, hypertension, hyperthyroidism, or hypothyroidism not controlled by diet or medication. Individuals having multiple health conditions may be excluded from participation even if controlled.
Started a long-term medication within the last 2 months.
Planned surgeries or invasive medical procedures during study.
Currently participating in any other clinical trial.
Participated in any clinical trial involving the face within 2 weeks prior to inclusion into the study.
Started hormone replacement therapies (HRT) or hormones for birth control less than 3 months prior to study entry or who plan on starting, stopping, or changing doses of HRT or hormones for birth control during study.

TABLE 3

Summary of Demographic Information

| | |
| --- | --- |
| Total Number of Subjects | 31 |
| Age of Subjects (years) | |
| Mean | 57.9 |
| Standard Deviation | 6.1 |
| Minimum | 43 |
| Median | 59 |
| Maximum | 65 |
| Sex | Number (%) |
| Female | 31 (100.0) |
| Ethnicity | |
| Hispanic or Latino | 3 (9.7) |
| Not Hispanic or Latino | 28 (90.3) |

TABLE 3-continued

Summary of Demographic Information

| Race | |
|---|---|
| American Indian or Alaska Native | 1 (3.2) |
| Asian | 3 (9.7) |
| Black or African American | 3 (9.7) |
| White or Caucasian | 24 (77.4) |
| Fitzpatrick skin type | |
| I | 2 (6.5) |
| II | 4 (12.9) |
| III | 16 (51.6) |
| IV | 6 (19.4) |
| V | 3 (9.7) |

The subjects were instructed to avoid application of any topical moisturizing products to the face for at least two days prior to the first visit. For the duration of the 12-week study, the subjects were instructed to cleanse their face twice daily (morning and evening) with a provided supporting cleanser, apply a provided sunscreen in the morning with reapplication as needed, and apply the test material (CE-GTP Serum) twice daily (morning and evening). The subjects were also instructed to refrain from extended periods of sun exposure and use of tanning beds and sunless tanning products, mechanical/chemical cleansers and devices on the face for the duration of the study, antiaging products, and new facial products other than the assigned CE-GTP Serum for the duration of the study. The subjects were allowed to continue use of all regular brands of color cosmetics, makeup remover, and sunscreen.

Outcome Measures

Clinical grading of efficacy parameters was conducted at visit 1 (baseline), visit 2 (week 4), visit 3 (week 8), and visit 4 (week 12). During each post-baseline visit, i.e. visits 2, 3 and 4, safety evaluations and VISIA-CR imaging were performed. For efficacy parameters, a modified Griffiths 10-point scale was used to clinically grade each subject for fine lines on the eye area, wrinkles on the global face and eye area, skin smoothness, hyperpigmentation, radiance, firmness, and overall photodamage on the global face. The skin smoothness and firmness were evaluated as a visual test. The clinical grading of efficacy parameters using the Modified Griffiths 10-point scale is presented in Table 4.

Safety was evaluated by clinically assessing the signs of erythema, edema, dryness and scaling. The subjects also evaluated safety of the CE-GTP composition by self-assessing the degree of burning, stinging, and itching globally. The safety evaluation is presented in Table 5.

TABLE 4

Clinical Grading of Efficacy Parameters Using Modified Griffiths 10-Point Scale

| Parameter | Location(s) | 0= | 9= |
|---|---|---|---|
| Fine lines | Eye area | None | Numerous, deep fine lines |
| Wrinkles | Global face Eye area | None | Numerous deep wrinkles |
| Skin smoothness (visual) | Global face | Smooth, even-looking skin texture, no roughness | Rough, uneven-looking skin texture |
| Hyperpigmentation | Global face | Even skin color, no hyperpigmentation | Significant (severe) hyperpigmented appearance, involving most of the face, with very strong intensity |
| Radiance | Global face | Radiant, luminous or glowing appearance | Dull/matte and/or sallow skin appearance |
| Firmness (visual) | Global face | Lifted, tight-appearing skin | Sagging, loose-appearing skin |
| Overall photodamage | Global face | None or minimal visual evidence of photodamaged skin | Severe photodamaged skin |

TABLE 5

Safety Evaluation Using a 4-Point Scale for Objective and Subjective (Self-Assessed) Irritation Parameters

| Parameter | 0 = None | 3 = Severe |
|---|---|---|
| Objective Irritation Parameters | | |
| Erythema | No erythema of treatment area | Marked redness of treatment area |
| Edema | No edema/swelling of treatment area | Marked edema of treatment area |
| Dryness | No dryness of treatment area | Marked dryness of treatment area |
| Scaling | No scaling of treatment area | Scaling a peeling of skin over all areas of treatment area |
| Subjective Irritation Parameters | | |
| Burning | No burning of treatment area | Hot burning sensation of treatment area that causes definite discomfort and may interrupt daily activities and/or sleep |
| Stinging | No stinging of treatment area | Marked stinging sensation of treatment area that causes definite discomfort and may interrupt daily activities and/or sleep |
| Itching | No itching of treatment area | Marked itching sensation of treatment area that causes definite discomfort and may interrupt daily activities and/or sleep |

Digital images were taken of each subject's face (left, center, and right views) using the VISA-CR photo station (Canfield Imaging Systems, Fairfield, NJ) with a Canon Mark II digital SLR camera (Canon Incorporated, Tokyo, Japan) under the following lighting conditions: standard 1 (visible [bright]), standard 2 (visible), standard 3 (raking light for crow's feet area), cross-polarized, and parallel polarized. Ultrasound measurements were also taken at the baseline visit and week 12 visit, i.e. visit 1 and visit 4. A single measurement was taken on the left crow's feet area using a 50 MHz ultrasonic transducer interfaced to a DUB 6100 OEM System (Taberna Pro Medicum, Lüneburg, Germany) to measure the skin density. The subjects reported outcomes were measured via self-assessment questionnaires at weeks 4, 8 and 12 to evaluate the subject perceived treatment outcomes and product performance.

Compliance

The subjects completed a daily diary, recording test material applications, adverse events, and comments during the study. The diaries were reviewed for compliance at each post-baseline visit. The provided CE-GTP Composition volumes were visually inspected at each post-baseline study visit to assess treatment compliance. Additionally, test material units were weighed prior to distribution and at weeks 4, 8, and 12 to quantify usage of the CE-GTP Serum by the subjects.

Statistical Analysis

The descriptive statistical summary for all efficacy grading parameters, safety evaluation parameters, and ultrasound measurements, included the N, mean, median, SD, MIN, and MAX of scores/values at all applicable time points. Mean of the change from baseline (defined as post-baseline value minus baseline value) was estimated at post-baseline time points. The null hypothesis, that the mean change from baseline was zero, was tested using the Wilcoxon signed rank test for the efficacy and safety results. The paired t test was used for comparing the ultrasound measurements.

Questionnaires were tabulated and the frequency and percentage of all response options were reported for each question and time point. A binomial (sign) test was performed to test if the proportion of the combined designated favorable responses was equal to the combined designated unfavorable responses for each applicable question.

All statistical tests were 2-sided at significance level alpha=0.05 unless specified otherwise. No multiple testing corrections were considered in the study. Statistical analyses were performed using SAS software version 9.4 (SAS Statistical Institute).

A total of 31 subjects were included in the intent-to-treat (ITT) population, with 30 subjects completing study participation. Data for discontinued subject 003 (baseline through week 8) was included in the statistical analyses as part of the ITT population. This study was conducted in accordance with federal regulations and Good Clinical Practice guidelines.

Clinical Grading of Efficacy Parameters

The clinical grading of efficacy parameters was analyzed and showed a statistically significant improvement (decrease) in scores at weeks 4, 8, and 12 when compared with baseline scores for fine lines on the eye area, skin smoothness, and radiance. Regarding scores for fine lines on the eye area, the mean change was −0.55±0.42, −0.77±0.59, and −1.20±0.77, with a % mean change of −16.6%, −23.4%, −36.2% at weeks 4, 8, and 12, respectively (p=<0.001, <0.001, <0.001, respectively). For skin smoothness scores there was a mean change of −0.29±0.25, −0.52±0.30, and −0.65±0.27 and % mean change of −6.2%, −11.1%, −13.9% at weeks 4, 8, and 12, respectively (p=<0.001, <0.001, <0.001, respectively). For radiance scores there was a mean change of −0.24±0.25, −0.39±0.25, and −0.58±0.27 and % mean change of −4.9%, −7.9%, −11.9% at weeks 4, 8, and 12, respectively (p=<001, <0.001, <0.001, respectively). There was a statistically significant improvement in scores for wrinkles on the global face and eye area, hyperpigmentation, and firmness at weeks 8 and 12. The mean score change for wrinkles on the global face was −0.11±0.21 and −0.32±0.31 with a % mean change of −2.4% and −6.6% at weeks 8 and 12, respectively (p=0.016 and <0.001, respectively). The mean score change for wrinkles on the eye are was −0.19±0.31 and −0.30±0.34 with a % mean change of −4.1% and −6.4% at weeks 8 and 12, respectively (p=0.002 and <0.001, respectively). For hyperpigmentation scores, the mean change was −0.29±0.25 and −0.43±0.17 with a % mean change of −6.0% and −8.9% at weeks 8 and 12, respectively (p=<0.001 and <001). For firmness scores, the mean change was −0.24±0.25 and −0.38±0.22 with a % mean change of −5.0% and −7.9% at weeks 8 and 12, respectively (p=<0.001 and <0.001, respectively). There was a statistically significant improvement in overall photodamage scores at week 12. The mean change was −0.43±0.17 with a mean % change of −8.9% (p=<0.001). The results of the clinical grading efficacy parameters is illustrated in FIG. 1.

Figure 2:
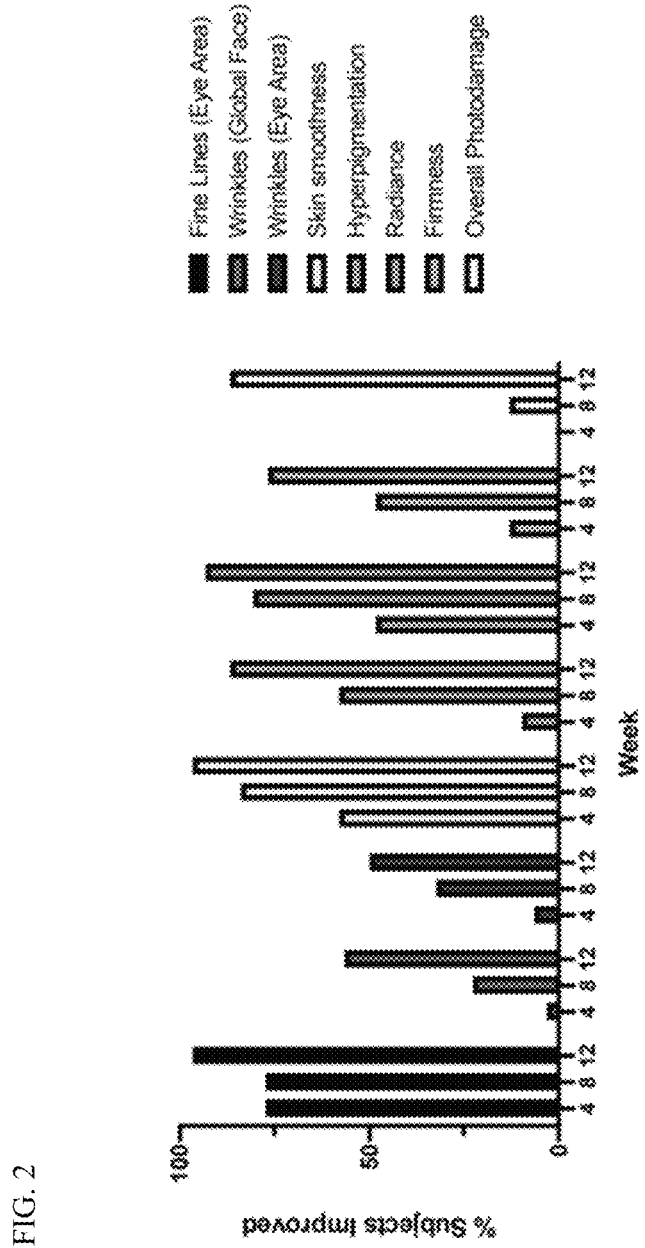
FIG. 2 is a summary of the clinically graded improvements experienced by subjects of the Clinical Study of Example 2.

For all efficacy parameters, by week 12, 50% or more of subjects displayed improvements. Of note, 96.7% of subjects demonstrated improvement in scores for fine lines on the eye area, 96.7% for smoothness, and 93.3% for radiance by week 12. FIG. 2 illustrates the percent of subjects with improvement at weeks 4, 8, and 12 for each efficacy parameter. No subjects displayed worsening in scores by week 12 in any of the efficacy parameters.

Safety Evaluations

The safety data was analyzed and demonstrated a statistically significant improvement (decrease) in scores for erythema on the global face at week 12 when compared with baseline scores (% mean change=−84.6, p=0.004). There was no statistically significant change (increase or decrease) in scores for dryness, scaling, burning, or stinging at any post-baseline time point when compared with baseline scores. Edema and itching were scored as 0 (none) at each time point.

No serious adverse events were reported. Of the 31 subjects in the study, only one experienced non-severe adverse effects, including pruritus and dry skin in the eye area and skin exfoliation in the forehead and mouth. These symptoms were temporary and resolved fully.

Ultrasound Measurements

Figure 3:
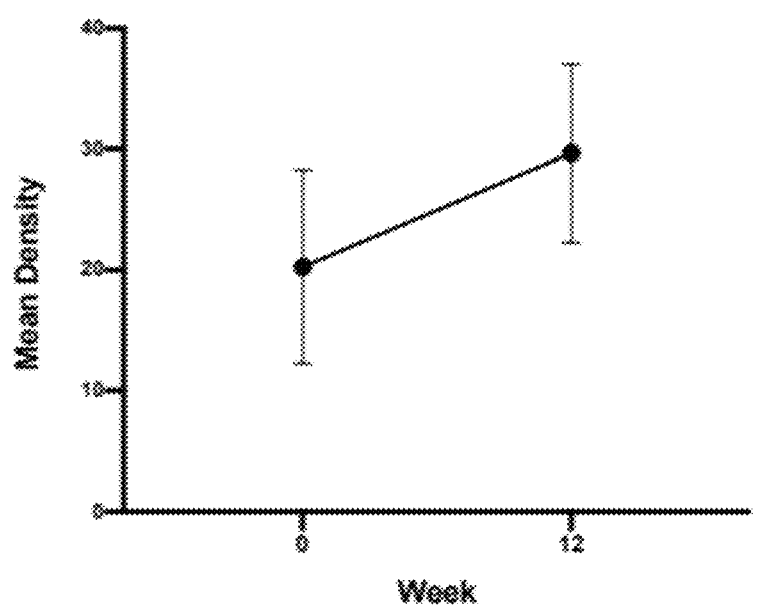
FIG. 3 is a summary of the ultrasound measurements of the Clinical Study of Example 2.

The Ultrasound measurements were analyzed and showed a statistically significant increase in skin density values at week 12 when compared with baseline values (% mean change=44.5, p=<0.001), indicating thickening of the epidermal and dermal tissue. The results are illustrated in FIG. 3.

From this study, it was demonstrated that the CE-GTP Serum is a safe and effective for improving photoaged facial skin. The CE-GTP Serum is able to correct hyperpigmentation and increase firmness, along with a wide variety of aesthetic concerns with a short duration of use. Remarkably, the majority of subjects displayed statistically significant improvement within 12 weeks across all clinical parameters. It was also notable that subjects demonstrated continued improvement across all clinical parameters throughout the duration of the study, which indicated that continued use yields continued aesthetic improvement.

The CE-GTP Composition quickly targets the periorbital area, which was evidenced by the majority of subjects showing statistically significant improvement in fine lines of the eye area within 4 weeks. Moreover, ultrasound measurements revealed a significant thickening of epidermal and dermal tissue in the crow's feet by week 12, resulting in younger, healthier skin.

The CE-GTP Composition satisfies the demand for an effective, natural personal skincare product. The subjects reported that the CE-GTP Serum was highly tolerable, non-irritating, and easy to use and apply, such that this vitamin and plant based product can be safely and easily incorporated into an at-home skincare routine.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Reference throughout this specification to numerical ranges should not be construed as limiting and should be understood as encompassing the outer limits of the range as well as each number and/or narrower range within the enumerated numerical range.

The term "about", when referring to a physical quantity, is to be understood to include measurement errors within, and inclusive of 10%. For example, "about 100° C." should be understood to mean "100±10° C.".

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A topical composition in the form of an emulsion of an aqueous phase and an oily phase, the emulsion comprising:
   an ascorbate component comprising ascorbic acid and tetrahexyldecyl ascorbate, wherein ascorbic acid is present in an amount ranging from about 10 wt. % to about 30 wt. % and tetrahexyldecyl ascorbate is present in an amount ranging from about 2 wt. % to about 15 wt. %, based on total weight of the topical composition; and
   above 0 wt. % and up to about 1 wt. % of an antioxidant system selected from green tea polyphenols, apigenin, ergothioneine, or combinations thereof, and
   wherein the topical composition comprises water in an amount of about 50 wt. % to about 60 wt. %, based on total weight of the topical composition.

2. The topical composition of claim 1, wherein the ascorbate component is present in the topical composition in an amount ranging from about 12 wt. % to about 40 wt. % based on total weight of the topical composition.

3. The topical composition of claim 1, wherein the ascorbic acid is present in the topical composition in an amount ranging from about 20 wt. % to about 30 wt. % based on total weight of the topical composition.

4. The topical composition of claim 1, wherein the weight ratio of ascorbic acid to tetrahexyldecyl ascorbate is from about 10:1 to about 1:1.5.

5. The topical composition of claim 1, wherein the green tea polyphenols are selected from epigallocatechin gallate, epigallocatechin, epicatechin gallate, catechin, epicatechin, or combinations thereof.

6. The topical composition of claim 1, further comprising additional antioxidants selected from the group of cinnamic acid, ferulic acid, caffeic acid, p-coumaric acid, sinapinic acid, cis and trans isomers thereof, salts thereof, and combinations thereof.

7. The topical composition of claim 1, wherein the topical composition is free of antioxidants selected from the group consisting of cinnamic acid, ferulic acid, caffeic acid, p-coumaric acid, m-coumaric acid, sinapinic acid, cis and trans isomers thereof, salts thereof, and combinations thereof.

8. The topical composition of claim 1, further comprising additional antioxidants selected from the group consisting of gallic acid, delphinidin, luteolin, quercetin, cyanidin, taxifolin, kaempferol, malvidin, hesperidin, pelargonidin, apigenin, naringenin, chrysin, ergothioneine, glutathione, emblica, cis and trans isomers thereof, salts thereof, and combinations thereof.

9. The topical composition of claim 1, wherein apigenin is present in an amount ranging from above 0 wt. % to about 0.5 wt. % based on total weight of the topical composition.

10. The topical composition of claim 1, wherein ergothioneine is present in an amount ranging from above 0 wt. % to about 0.5 wt. % based on total weight of the topical composition.

11. The topical composition of claim 1, wherein green tea polyphenols are present in an amount ranging from above 0 wt. % to about 0.5 wt. % based on total weight of the topical composition.

12. The topical composition of claim 6, wherein (i) green tea polyphenols are present in an amount ranging from above 0 wt. % to about 0.5 wt. % based on total weight of the topical composition; and (ii) the weight ratio of the green tea polyphenols to the additional antioxidants ranges from about 10:1 to about 1:10.

13. The topical composition of claim 1, further comprising a cosmetically acceptable excipient.

14. The topical composition of claim 13, wherein the cosmetically acceptable excipient is an epidermal penetration enhancer, solvent, surfactants, oil bodies, emulsifiers, pearlescent waxes, consistency regulators, thickeners, suspending agents, chelating agents, preservatives, superfatting agents, stabilizers, polymers, silicone compounds, fats, waxes, lecithins, phospholipids, UV photoprotective factors, biogenic active ingredients, additional antioxidants, deodorants, antiperspirants, film formers, swelling agents, insect repellents, self-tanning agents, tyrosinase inhibitors, hydrotropes, solubilizers, perfume oils, dyes, or combinations thereof.

15. The topical composition of claim 13, wherein the cosmetically acceptable excipient is a solvent, emulsifiers, consistency regulators, thickeners, suspending agent, preservative, additional antioxidants, perfume oils, or combinations thereof.

* * * * *